United States Patent
Howard et al.

(10) Patent No.: US 10,351,552 B2
(45) Date of Patent: Jul. 16, 2019

(54) BICYCLIC ANTIPARASITIC COMPOUNDS

(71) Applicants: Harry Ralph Howard, Bristol, CT (US); Dennis Michael Godek, Glastonbury, CT (US); Shawn-Michael Rodriguez, Wolcott, CT (US)

(72) Inventors: Harry Ralph Howard, Bristol, CT (US); Dennis Michael Godek, Glastonbury, CT (US); Shawn-Michael Rodriguez, Wolcott, CT (US)

(73) Assignee: MediSynergies, LLC, Farmington, CT (US)

(*) Notice: Subject to any disclaimer, the term of this patent is extended or adjusted under 35 U.S.C. 154(b) by 0 days.

(21) Appl. No.: 15/834,728

(22) Filed: Dec. 7, 2017

(65) Prior Publication Data

US 2019/0177304 A1    Jun. 13, 2019

(51) Int. Cl.
| | |
|---|---|
| *A61P 33/02* | (2006.01) |
| *C07D 405/04* | (2006.01) |
| *C07D 409/04* | (2006.01) |
| *C07D 413/04* | (2006.01) |
| *C07D 417/04* | (2006.01) |
| *A61K 31/343* | (2006.01) |

(52) U.S. Cl.
CPC .......... *C07D 405/04* (2013.01); *A61P 33/02* (2018.01); *C07D 409/04* (2013.01); *C07D 413/04* (2013.01); *C07D 417/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,284,291 B2* | 3/2016 | Godek | ................ | C07D 307/87 |
| 9,346,777 B2* | 5/2016 | Godek | ................ | C07D 405/04 |
| 9,475,788 B2* | 10/2016 | Godek | ................ | C07D 405/04 |
| 9,700,563 B2* | 7/2017 | Godek | ................ | C07D 405/04 |

OTHER PUBLICATIONS

Banala, AK et al "Design and Synthesis of 1-(3-Dimethylamino)propyl)-1-(4-fluorophenyl)-1,3-dihydroisobenzofuran-5-carbo . . . " Journal of Medicinal Chemistry (2013), 56:9709-24.
Zhang, P et al "Structure-Activity Relationships for a Novel Series of Citalopram . . . " Journal of Medicinal Chemistry (2010) 53:6112-6121.

* cited by examiner

*Primary Examiner* — Amanda L Aguirre

(57) ABSTRACT

The invention is directed to a compound of formula I, a pharmaceutically acceptable salt thereof, a pharmaceutical composition containing a compound of formula I, and a method of treatment of a disorder or condition in a mammal, including a human, selected from the group consisting of Human African Trypanosomiasis (HAT), Chagas disease, Leishmaniasis, toxoplasmosis and malaria.

16 Claims, No Drawings

BICYCLIC ANTIPARASITIC COMPOUNDS

STATEMENT REGARDING FEDERALLY SPONSORED RESEARCH

This invention was made with Government support under Grant No. R43AI122475-01 awarded by The National Institutes of Health (NIH). The government has certain rights in the invention.

BACKGROUND OF THE INVENTION

This invention is directed to compounds of the formula I described herein, to a pharmaceutical composition comprising such compounds and to methods of preventing or treating disorders or conditions that may be treated by administration of such compounds to a mammal in need, including humans. In particular, the compounds of the current invention are potentially useful for treating certain parasitic infections including human African trypanosomiasis (HAT), Chagas disease, Leishmaniasis, toxoplasmosis and malaria.

Human African Trypanosomiasis (HAT) is a disease spread by a parasitic organism, *trypanosoma brucei*, which is transmitted to humans primarily via bites from the tsetse fly—transmission may also occur via blood transfusion or in utero exposure of a fetus from an infected mother via the placenta. It is often referred to as "sleeping sickness" because of the symptoms that develop in patients who have progressed to the advanced, or Stage 2, level of infection wherein the parasite has passed the blood brain barrier (BBB) exposing the central nervous system (CNS) of the victim to further infection by the parasite. Left untreated, this latter stage of the disease is typically fatal (Jacobs and Ding, *Annual Reports in Medicinal Chemistry*, (2010) 45, 277-294; Rollo, Chapter 50 of *Goodman and Gilman's, The Pharmacological Basis of Therapeutics*, 12$^{th}$ Ed., 2011, 1419-1441).

The disease is found in two forms, depending on the parasite sub-species involved, either *Trypanosoma brucei gambiense* (T.b.g) or *Trypanosoma brucei rhodesiense* (T.b.r.). Humans are the primary host for *T. b. gambiense*, whereas wild game animals and cattle are the primary target of *T. b. rhodesiense*. *T. b. gambiense* is found in central and western Africa and causes a chronic condition that can remain in a passive phase for months or years before symptoms emerge. *T. b. rhodesiense* is found in southern and eastern Africa; symptoms of infection by *T. b. rhodesiense* generally emerge in a few weeks and are more virulent and faster developing than *T. b. gambiense*.

While approximately one-half million inhabitants of sub-Saharan Africa are potentially infected each year by the hemolymphatic, Stage 1, form of HAT, the number of HAT cases has been diminishing, with the World Health Organization (WHO) estimating an annual mortality of 10,000 (see P.P. Simarro, et al, *International Journal of Health Geographies*, 2010, 9, 57). However, this trend has varied over the years and, with few efficacious and cost effective preventative measures being consistently used, the number of cases could quickly rebound. Symptoms include fever, headaches, joint pains and itching, as well as severe swelling of lymph nodes. Chronically, HAT can produce more extensive symptoms including anemia, endocrine, cardiac and kidney dysfunctions.

The drugs that are available act directly on the invasive protozoa in the bloodstream; poor penetration of the blood-brain barrier (BBB) has limited the use of some of these drugs to treatment of the hemolymphatic, first stage of HAT. These include suramin, developed in the 1920's and primarily used for Stage 1 *T. b. rhodesiense* HAT; pentamidine, discovered in 1940, which requires multiple intramuscular (i.m.) injections and is only effective for Stage 1 HAT; melarsoprol (identified in 1949) which also requires multiple, painful daily injections and is highly toxic, often used for the most severely ill Stage 2 patients; and eflornithine, a drug developed in 1981 which requires slow i.v. infusions over a two-week period to ensure sufficient CNS exposure to treat *T. b. gambiense*-induced Stage 2 HAT. A nifurtimox-eflornithine combination therapy (NECT) was created in 2009; it appears to be better tolerated for Stage 2 HAT patients (see Nok, *Expert Opinion in Pharmacotherapy*, 2005, 6(15):2645-2653).

Of growing concern in recent years is the issue of cross-resistance to some of these medications. This has been observed with pentamidine and arsenicals like melarsoprol (de Koning, *Trends in Parasitology*, 2008, 24(8):345-349).

Interestingly, the organism that is responsible for HAT, *T. brucei*, is related to other parasitic species that can cause severely debilitating diseases in humans and animals. Chagas disease, caused by the related parasite *T. cruzi*, is prevalent in South America, affecting up to 10 million individuals. It has also been detected in cattle; human fatalities from Chagas are estimated to be 21,000 per year.

Leishmaniases in their various manifestations—cutaneous Leishmaniasis (via *L. major, L. mexicana, L. aethiopica, L. tropica*), mucocutaneous leishmaniasis (*L. braziliensis*) and visceral leishmaniasis (*L. donovani/infantum*) are estimated to affect nearly 2 million people on four continents.

Toxoplasmosis, a parasitic disorder spread by *Toxoplasma gondii*, may be present in contaminated foods and cat feces. It is most serious for pregnant women and patients whose immune systems have been compromised, but is generally benign in most healthy humans. (See Silva, et al, *Biochemical Pharmacology*, 2007, 73:1939-1946).

One of the most commonly used HAT treatments for Stage 1 is pentamidine. This diamidine compound has been extensively studied with respect to structure-activity relative to the replacement of its 1,5-dioxopentyl section by a variety of aryl and heteroaryl rings (See, e.g., R. R. Tidwell, et al, in *Journal of Medicinal Chemistry*, 2006, 49:5324; *Journal of Medicinal Chemistry*, 2007, 50:2468; *Journal of Medicinal Chemistry*, 2008, 51:6923; *Journal of Medicinal Chemistry*, 2009, 52:5763; *Journal of Medicinal Chemistry*, 2010, 53:254). Little research has been done to enhance pentamidine's brain concentration through the incorporation into the molecule of CNS-penetration enhancing groups, such as those found in some effective antipsychotic and antidepressant drugs currently on the market.

It is possible that any new treatment for HAT which targets *T. brucei* parasites could also have sufficient efficacy against related parasitic species and, therefore would be a valuable improvement in antiparasitic therapy.

SUMMARY OF THE INVENTION

This invention is directed to compounds of the formula I:

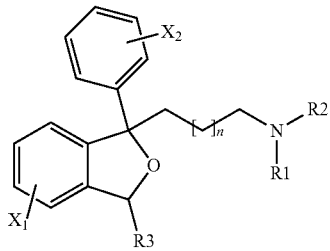

or to a pharmaceutically acceptable salt(s) thereof, wherein:

$X_1$ is a bicyclic heteroaryl group selected from the list consisting of benzimidazolyl, benzothiazolyl, benzoxazolyl, benzisoxazolyl benzothiophenyl, indolyl, indazolinyl, quinolinyl, isoquinolinyl, quinazolinyl, quinoxalinyl, phthalazinyl, benzisothiazolyl and benzofuranyl;

$X_2$ is H, CI or F;

R1 and R2 are independently hydrogen or methyl;

R3 is hydrogen; and n is zero, one or two.

The invention is also directed to a pharmaceutical composition for treating a disorder or condition selected from human African trypanosomiasis, Chagas disease, Leishmaniasis, toxoplasmosis and malaria in a mammal, including a human, that may be treated by administering to a mammal in need of such treatment a compound of formula I as described above, or a pharmaceutically acceptable salt thereof, that is effective in treating such disorder or condition, and a pharmaceutically acceptable carrier.

The invention is also directed to a method of treatment of a disorder or condition selected from the group consisting of the disorders or conditions listed in the preceding paragraph, the method comprising administering to said mammal in need of such treatment an amount of a compound of formula I as described above that is effective in treating such disorder or condition.

The invention also relates to the use of a compound of the formula I, or a pharmaceutically acceptable salt thereof, in the manufacture of a medicament for the treatment of a disorder or condition, the treatment of which can be effected or facilitated by administration of an effective amount of the medicament to a mammal, including a human, in need of such treatment.

The most preferred embodiment of the present invention includes the compounds of formula I in which:

R1 and R2 are methyl;

R3 is hydrogen;

$X_1$ is a bicyclic heteroaryl ring as previously defined;

$X_2$ is 4-fluoro; and n is one.

Preferred embodiments of the present invention include the compounds of formula I in which:

R1 and R2 are independently methyl;

$X_1$ is a bicyclic heteroaryl group as previously defined; and n is one.

The most preferred compounds of the invention include:

3-[1-(4-fluorophenyl)-5-(1,3-benzoxazol-5-yl)-1,3-dihydro-2-benzofuran-1-yl]-N,N-dimethylpropan-1-amine;

3-[1-(4-fluorophenyl)-5-(5-methyl-1,3-benzoxazol-2-yl)-1,3-dihydro-2-benzofuran-1-yl]-N,N-dimethylpropan-1-amine;

3-[1-(4-fluorophenyl)]-[5-(1-benzo[b]thiophen-2-yl)-1,3-dihydro-2-benzofuran-1-yl]-N,N-dimethylpropan-1-amine; and 3-[1-(4-fluorophenyl)-5-(1,3-benzothiazol-5-yl)-1,3-dihydro-2-benzo-furan-1-yl]-N,N-dimethylpropan-1-amine.

Other preferred compounds of the invention include:

3-[1-(4-fluorophenyl)-5-(5-methyl-1,3-benzoxazol-2-yl)-1,3-dihydro-2-benzofuran-1-yl]-N,N-dimethylpropan-1-amine;

3-[1-(4-fluorophenyl)-5-(5,6-dimethyl-1,3-benzoxazol-2-yl)-1,3-dihydro-2-benzofuran-1-yl]-N,N-dimethylpropan-1-amine;

3-[1-(4-fluorophenyl)-5-(5-ethyl-1,3-benzoxazol-2-yl)-1,3-dihydro-2-benzofuran-1-yl]-N,N-dimethylpropan-1-amine;

3-[1-(4-fluorophenyl)-5-(5-fluoro-1,3-benzoxazol-2-yl)-1,3-dihydro-2-benzofuran-1-yl]-N,N-dimethylpropan-1-amine;

3-[1-(4-fluorophenyl)-5-(5-trifluoromethyl-1,3-benzoxazol-2-yl)-1,3-dihydro-2-benzofuran-1-yl]-N,N-dimethylpropan-1-amine;

3-[1-(4-fluorophenyl)-5-(5-methoxy-1,3-benzoxazol-2-yl)-1,3-dihydro-2-benzofuran-1-yl]-N,N-dimethylpropan-1-amine;

3-[1-(4-fluorophenyl)]-[5-(3-methyl-1-benzo[b]thiophen-2-yl)-1,3-dihydro-2-benzofuran-1-yl]-N,N-dimethylpropan-1-amine;

3-[1-(4-fluorophenyl)]-[5-(5,6-dimethyl-1-benzo[b]thiophen-2-yl)-1,3-dihydro-2-benzofuran-1-yl]-N,N-dimethylpropan-1-amine;

3-[1-(4-fluorophenyl)]-[5-(5-methoxyl-1-benzo[b]thiophen-2-yl)-1,3-dihydro-2-benzofuran-1-yl]-N,N-dimethylpropan-1-amine;

3-[1-(4-fluorophenyl)]-[5-(6-nitro-1-benzo[b]thiophen-2-yl)-1,3-dihydro-2-benzofuran-1-yl]-N,N-dimethylpropan-1-amine;

3-[1-(4-fluorophenyl)]-[5-(5-cyano-1-benzo[b]thiophen-2-yl)-1,3-dihydro-2-benzofuran-1-yl]-N,N-dimethylpropan-1-amine;

3-[1-(4-fluorophenyl)]-[5-(4,7-dimethyl-1-benzo[b]thiophen-2-yl)-1,3-dihydro-2-benzofuran-1-yl]-N,N-dimethylpropan-1-amine;

3-[1-(4-fluorophenyl)-5-(2-methyl-1,3-benzothiazol-5-yl)-1,3-dihydro-2-benzofuran-1-yl]-N,N-dimethylpropan-1-amine;

3-[1-(4-fluorophenyl)-5-(2-phenyl-1,3-benzothiazol-5-yl)-1,3-dihydro-2-benzofuran-1-yl]-N,N-dimethylpropan-1-amine;

3-[1-(4-fluorophenyl)-5-(6,7-dimethyl-1,3-benzothiazol-5-yl)-1,3-dihydro-2-benzofuran-1-yl]-N,N-dimethylpropan-1-amine;

3-[1-(4-fluorophenyl)-5-(7-nitro-1,3-benzothiazol-5-yl)-1,3-dihydro-2-benzofuran-1-yl]-N,N-dimethylpropan-1-amine;

3-[1-(4-fluorophenyl)-5-(1,3-benzothiazol-5-yl)-1,3-dihydro-2-benzo-furan-1-yl]-N,N-methylpropan-1-amine;

3-[1-(4-fluorophenyl)-5-(6-trifluoromethyl-1,3-benzoxazol-5-yl)-1,3-dihydro-2-benzofuran-1-yl]-N,N-dimethylpropan-1-amine;

3-[1-(4-fluorophenyl)-5-(6-methoxy-1,3-benzoxazol-5-yl)-1,3-dihydro-2-benzofuran-1-yl]-N,N-dimethylpropan-1-amine;

3-[1-(4-fluorophenyl)-5-(4,7-dimethyl-1,3-benzoxazol-5-yl)-1,3-dihydro-2-benzofuran-1-yl]-N,N-dimethylpropan-1-amine;
3-[1-(4-fluorophenyl)-5-(6-chloro-1,3-benzoxazol-5-yl)-1,3-dihydro-2-benzofuran-1-yl]-N,N-dimethylpropan-1-amine;
3-[1-(4-fluorophenyl)-5-(6-fluoro-1,3-benzoxazol-5-yl)-1,3-dihydro-2-benzofuran-1-yl]-N,N-dimethylpropan-1-amine;
3-[1-(4-fluorophenyl)-5-(1H-indol-5-yl)-1,3-dihydro-2-benzofuran-1-yl]-N,N-dimethylpropan-1-amine;
3-[1-(4-fluorophenyl)-5-(1-methyl-1H-indol-5-yl)-1,3-dihydro-2-benzofuran-1-yl]-N,N-di-methylpropan-1-amine;
3-[1-(4-fluorophenyl)-5-(5-methoxy-1H-indol-2-yl)-1,3-dihydro-2-benzofuran-1-yl]-N,N-dimethylpropan-1-amine;
3-[1-(4-fluorophenyl)-5-(6-chloro-1H-indol-1-yl)-1,3-dihydro-2-benzofuran-1-yl]-N,N-dimethylpropan-1-amine;
3-[1-(4-fluorophenyl)-5-(7-methyl-1H-indol-4-yl)-1,3-dihydro-2-benzofuran-1-yl]-N,N-di-methylpropan-1-amine;
3-[1-(4-fluorophenyl)-5-(6,7-dichloro-1H-indol-4-yl)-1,3-dihydro-2-benzofuran-1-yl]-N,N-dimethylpropan-1-amine;
3-[1-(4-fluorophenyl)-5-(5-methyl-1H-indol-4-yl)-1,3-dihydro-2-benzofuran-1-yl]-N,N-dimethylpropan-1-amine;
3-[1-(4-fluorophenyl)]-5-[(1-benzo[b]thiophen-2-yl)]-1,3-dihydro-2-benzofuran-1-yl]-N,N-dimethylpropan-1-amine;
3-[1-(4-fluorophenyl)]-5-[(3-methyl-1-benzo[b]thiophen-2-yl)]-1,3-dihydro-2-benzofuran-1-yl]-N,N-dimethylpropan-1-amine;
3-[1-(4-fluorophenyl)]-5-[(5,6-dimethyl-1-benzo[b]thiophen-2-yl)]-1,3-dihydro-2-benzofuran-1-yl]-N,N-dimethylpropan-1-amine;
3-[1-(4-fluorophenyl)]-5-[(5-methoxy-1-benzo[b]thiophen-2-yl)]-1,3-dihydro-2-benzofuran-1-yl]-N,N-dimethylpropan-1-amine;
3-[1-(4-fluorophenyl)]-5-[(5,6-difluoro-1-benzo[b]thiophen-2-yl)]-1,3-dihydro-2-benzofuran-1-yl]-N,N-dimethylpropan-1-amine;
3-[1-(4-fluorophenyl)]-[5-(1-methyl-1H-indol-5-yl)-1,3-dihydro-2-benzofuran-1-yl]-N,N-dimethylpropan-1-amine;
3-[1-(4-fluorophenyl)]-[5-(1-ethyl-1H-indol-5-yl)-1,3-dihydro-2-benzofuran-1-yl]-N,N-dimethylpropan-1-amine;
3-[1-(4-fluorophenyl)]-[5-(1-isopropyl-1H-indol-5-yl)-1,3-dihydro-2-benzofuran-1-yl]-N,N-dimethylpropan-1-amine;
3-[1-(4-fluorophenyl)]-[5-(1,3-dimethyl-1H-indol-5-yl)-1,3-dihydro-2-benzofuran-1-yl]-N,N-dimethylpropan-1-amine;
3-[1-(4-fluorophenyl)]-[5-(7-chloro-1-methyl-1H-indol-5-yl)-1,3-dihydro-2-benzofuran-1-yl]-N,N-dimethylpropan-1-amine;
3-[1-(4-fluorophenyl)]-[5-(quinolin-3-yl)-1,3-dihydro-2-benzofuran-1-yl]-N,N-dimethylpropan-1-amine;
3-[1-(4-fluorophenyl)]-[5-(2-methyl-quinolin-3-yl)-1,3-dihydro-2-benzo-furan-1-yl]-N,N-dimethylpropan-1-amine;
3-[1-(4-fluorophenyl)]-[5-(6,7-dichloro-quinolin-3-yl)-1,3-dihydro-2-benzofuran-1-yl]-N,N-dimethylpropan-1-amine;
3-[1-(4-fluorophenyl)]-[5-(7,8-dimethoxy-quinolin-3-yl)-1,3-dihydro-2-benzofuran-1-yl]-N,N-propan-1-amine;
3-[1-(4-fluorophenyl)]-[5-(7-methyl-quinolin-3-yl)-1,3-dihydro-2-benzo-furan-1-yl]-N,N-methylpropan-1-amine;
3-[1-(4-fluorophenyl)]-[5-(7-nitro-quinolin-3-yl)-1,3-dihydro-2-benzo-furan-1-yl]-N,N-dimethylpropan-1-amine;
3-[1-(4-fluorophenyl)]-[5-(1-methyl-isoquinolin-4-yl)-1,3-dihydro-2-benzofuran-1-yl]-N,N-dimethylpropan-1-amine;
3-[1-(4-fluorophenyl)]-[5-(6,7-difluoro-isoquinolin-4-yl)-1,3-dihydro-2-benzofuran-1-yl]-N,N-dimethylpropan-1-amine;
3-[1-(4-fluorophenyl)]-[5-(7-methyl-isoquinolin-4-yl)-1,3-dihydro-2-benzofuran-1-yl]-N,N-dimethylpropan-1-amine; 3-[1-(4-fluorophenyl)]-[5-(5,8-dimethyl-isoquinolin-4-yl)-1,3-dihydro-2-benzofuran-1-yl]-N,N-dimethylpropan-1-amine;
3-[1-(4-fluorophenyl)]-[5-(isoquinolin-4-yl)-1,3-dihydro-2-benzofuran-1-yl]-N,N-methylpropan-1-amine;
3-[1-(4-fluorophenyl)-5-(1,3-benzimidazol-2-yl)-1,3-dihydro-2-benzo-furan-1-yl]-N,N-dimethylpropan-1-amine;
3-[1-(4-fluorophenyl)-5-(1,3-benzimidazol-5-yl)-1,3-dihydro-2-benzo-furan-1-yl]-N,N-dimethylpropan-1-amine;
3-[1-(4-fluorophenyl)-5-(1,2-benzisoxazol-2-yl)-1,3-dihydro-2-benzo-furan-1-yl]-N,N-dimethylpropan-1-amine;
3-[1-(4-fluorophenyl)-5-(1,2-benzisoxazol-5-yl)-1,3-dihydro-2-benzo-furan-1-yl]-N,N-dimethylpropan-1-amine;
3-[1-(4-fluorophenyl)-5-(1,2-indazol-3-yl)-1,3-dihydro-2-benzofuran-1-yl]-N,N-dimethylpropan-1-amine;
3-[1-(4-fluorophenyl)-5-(1,2-indazol-5-yl)-1,3-dihydro-2-benzofuran-1-yl]-N,N-dimethylpropan-1-amine;
3-[1-(4-fluorophenyl)-5-(1,2-indazol-6-yl)-1,3-dihydro-2-benzofuran-1-yl]-N,N-dimethylpropan-1-amine;
3-[1-(4-fluorophenyl)-5-(1,3-quinazol-2-yl)-1,3-dihydro-2-benzofuran-1-yl]-N,N-dimethylpropan-1-amine;
3-[1-(4-fluorophenyl)-5-(1,3-quinazol-4-yl)-1,3-dihydro-2-benzofuran-1-yl]-N,N-dimethylpropan-1-amine;
3-[1-(4-fluorophenyl)-5-(1,3-quinazol-6-yl)-1,3-dihydro-2-benzofuran-1-yl]-N,N-dimethylpropan-1-amine;
3-[1-(4-fluorophenyl)-5-(1,3-quinazol-7-yl)-1,3-dihydro-2-benzofuran-1-yl]-N,N-dimethylpropan-1-amine;
3-[1-(4-fluorophenyl)-5-(1,4-quinoxalin-2-yl)-1,3-dihydro-2-benzofuran-1-yl]-N,N-dimethylpropan-1-amine;
3-[1-(4-fluorophenyl)-5-(1,4-quinoxalin-6-yl)-1,3-dihydro-2-benzofuran-1-yl]-N,N-dimethylpropan-1-amine;
3-[1-(4-fluorophenyl)-5-(1,4-quinoxalin-7-yl)-1,3-dihydro-2-benzofuran-1-yl]-N,N-dimethylpropan-1-amine;
3-[1-(4-fluorophenyl)-5-(1,2-benzisothiazol-3-yl)-1,3-dihydro-2-benzo-furan-1-yl]-N,N-dimethylpropan-1-amine;
3-[1-(4-fluorophenyl)-5-(1,2-benzisothiazol-5-yl)+1,3-dihydro-2-benzo-furan-1-yl]-N,N-dimethylpropan-1-amine;
3-[1-(4-fluorophenyl)-5-(1,2-benzisothiazol-6-yl)+1,3-dihydro-2-benzo-furan-1-yl]-N,N-dimethylpropan-1-amine; and
3-[1-(4-fluorophenyl)-5-(1,2-benzisothiazol-7-yl)+1,3-dihydro-2-benzo-furan-1-yl]-N,N-dimethylpropan-1-amine.

A preferred use for the compounds of formula I is in the treatment of human African trypanosomiasis (HAT). Other preferred uses for the compounds of formula I are in the treatment of Chagas disease, Leishmaniasis, toxoplasmosis and malaria.

DETAILED DESCRIPTION OF THE INVENTION

The compounds of formula I may be prepared as described in the following reaction schemes and discussions. Unless otherwise indicated, $X_1$, $X_2$, R1, R2, R3 and n, and structural formulae II, III and IV in the reaction schemes and discussion that follow are as defined above.

The starting materials for these processes, compounds of the general formula II-IV (Schemes 1-3, below) are available using procedures described in the chemical and patent literature or are commercially available. For example, the compound of formula II, (i.e., formula I, wherein n=1, R1=CH$_3$, R2=CH$_3$, R3=H, $X_2$ is 4-fluoro and $X_1$ is a cyano (i.e., CN) group attached at the 5-position of the benzofuran ring is available as the antidepressant drug citalopram (Celexa™) in racemic form or as the(S)-isomer antidepressant medication escitalopram (Lexapro™). Procedures for the conversion of the compounds of formula II to formula I are readily available in the literature (e.g., see M. Pitts, *Tetrahedron*, 2006, 62, 4705-4708; N. Periyandi, et al, PCT Int. Appl., 2006, WO-2006021971; T. Ikemoto and Y. Watanabe, PCT Int. Appl., 2005, WO-2005082842; H. Ahmadian and H. Petersen, PCT Int. Appl., 2003, WO-2003051861; H. Petersen, PCT Int. Appl. 2001, WO-2001068631; L. Dall'Asta, et al, PCT Int. Appl., (2000), WO-2000023431).

The intermediate compounds of formula III, (i.e., formula I, wherein n=1, R1=CH$_3$, R2=CH$_3$, R3=H, $X_2$ is 4-fluoro and $X_1$ is an aldehyde group attached at the 5-position of the benzofuran ring can be prepared directly from a cyano compound of formula II by treatment with a selective reagent such as Raney nickel in formic acid (see *Organic Synthesis*, 1988, Collective Vol. 6, p 631). Other methods include the use of diisobutylaluminum hydride (DIBAL-H), (e.g., Munoz J M, Alcazar J, et al, *Tetrahedron Letters*, 2011, 52:6058-6060) and reductive hydrolysis using ruthenium or platinum-loaded zeolites (Chatterjee A, Shaikh R A, Raj A, Singh A P, *Catalysis Letters*, 1995, 31(2-3):301-305).

The intermediate compounds of formula IV, (i.e., formula I, wherein n=1, R1=CH$_3$, R2=CH$_3$, R3=H, $X_2$ is 4-fluoro and X1 is a bromine atom) can be prepared according to the procedure of Zhang P, Cyriac G, KopajticT, Zhao Y, Javitch J, Katz J L and Newman A H, "Structure-Activity Relationships for a Novel Series of Citalopram (1-(3-(Dimethylamino)-propyl)-1-(4-fluorophenyl)-1,3-dihydroisobenzofuran-5-carbonitrile) Analogues at Monoamine Transporters" *Journal of Medicinal Chemistry*, 2010, 53:6112-6121. The reference also describes preparation of the individual R- and S-isomers of IV.

Scheme 1

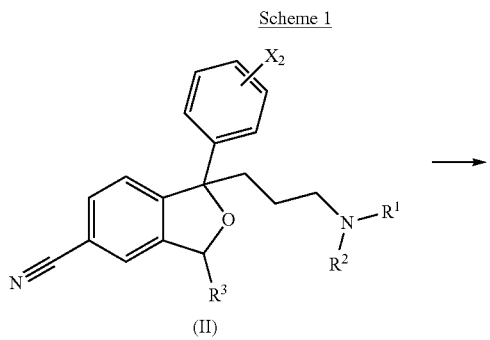

(II)

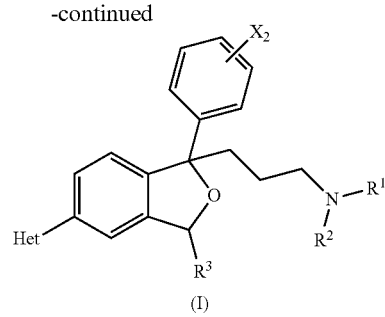

(I)

In one embodiment, an intermediate nitrile of the general formula II (i.e., formula I, wherein $X_1$ is —CN) can be converted into a compound of the general formula I wherein $X_1$ is a heteroaryl group, using one or more of a variety of methods described in the chemical literature (Scheme 1 above). Examples in the literature include: Sluiter J, Christoffers J, *Synlett*, 2009, 63-66; Sun Y, Jiang H, Wu W, et al, *Organic Letters*, 2013, 15:1598-1601.

Scheme 2

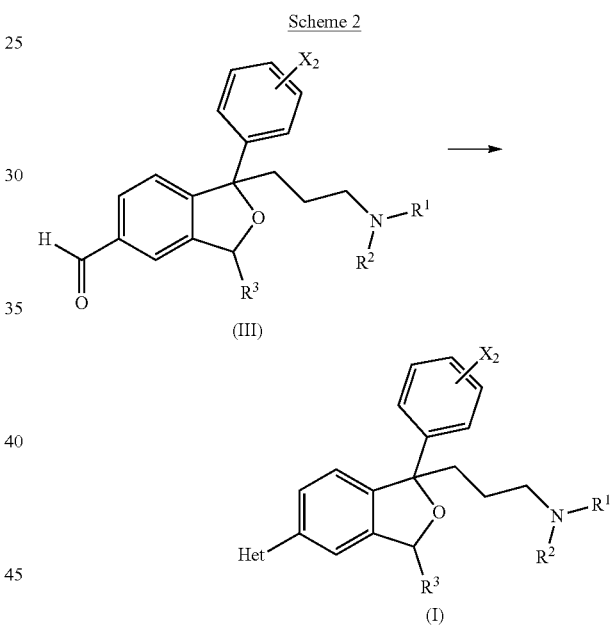

In another embodiment, an intermediate aldehyde of the general formula III (i.e., formula I, wherein $X_1$ is —CHO) can be converted into a compound of the general formula I wherein $X_1$ is a heteroaryl group, using one or more of a variety of methods described in the chemical literature (Scheme 2, above). Examples of such conversions are numerous in the patent and chemical literature, e.g., Gorepatil P B, Mane Y D, Ingle V S, *Synlett*, 2013, 24:2241-2244; Hu R, Li X, Tong Y, et al, *Synlett*, 2016, 27:1387-1390; Yang Z, Chen X, Wang S, et al, *Journal of Organic Chemistry*, 2012, 77:7086-7091; Bahrami K, Khodaei M M, Naali F, *Journal of Organic Chemistry*, 2008, 73:6835-6837; Zhu C, Akiyama T, *Synlett*, 2010, 2345-2351; Liu J, Gui Q, Zang Z et al, *Synthesis*, 2013, 45:943-951; Mahesh D, Sadhu P, Punniyamurthy T, *Journal of Organic Chemistry*, 2015, 80:1644-1650; Kim Y, Kumar M R, Park N et al, *Journal of Organic Chemistry*, 2011, 76:9577-9583; Bahrami K, Khodaei M M, Kavianinia I, *Synthesis*, 2007, 417-427; Du L-H, Wang Y-G, *Synthesis*, 2007, 675-678.

Scheme 3

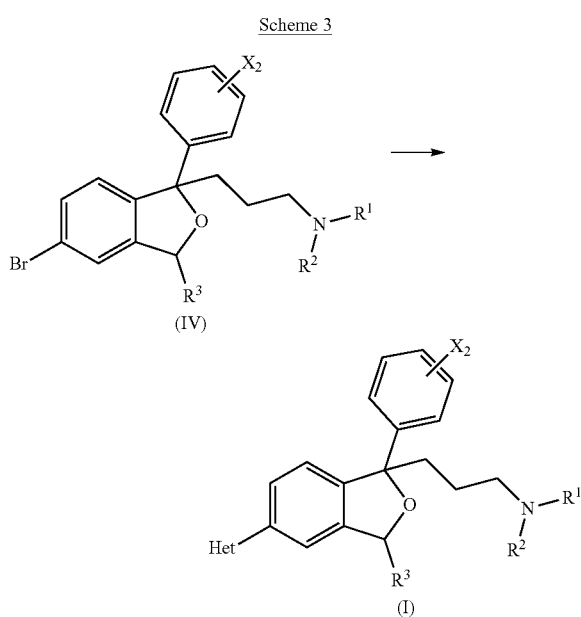

In yet another embodiment, an intermediate of the general formula IV (wherein $X_3$ is a chlorine, bromine or iodine atom) can be converted into a compound of the general formula I wherein $X_1$ is a heteroaryl group, using one or more of a variety of methods described in the chemical literature (Scheme 3 above). The starting materials for this process, compounds of the general formula IV, wherein $X_1$ is chlorine, bromine or iodine, are described in the chemical literature, or may be commercially available (e.g., see J. Eildal, et al, *Journal of Medicinal Chemistry*, 2008, 51:3045). The heteroaryl boronic acids or esters may be obtained from commercial sources (e.g., Sigma-Aldrich Chemical, St. Louis, Mo.), or prepared as described in the chemical literature (e.g., see P. Bartlett, et al, *Chemical Reviews*, 1997, 97:1281; R. Batey, et al, *Journal of the American Chemical Society*, 1999, 121:5075; J. Bird, et al, *Journal of Medicinal Chemistry*, 1994, 37:158). The conversion can be accomplished via a process referred to as a Suzuki (or Suzuki-Miyaura) coupling reaction (see K. Wong, et al, *Journal of Organic Chemistry*, 2002, 67(3): 1041-1044). The reaction typically employs a palladium catalyst to couple an aryl halide with a heteroaryl boronic acid or boronate ester. Examples of this reaction can be found in, for example, L. Zhang, et al, *Journal of Medicinal Chemistry*, 2010, 53(16):6112-6121; L. Wang, et al, *European Journal of Organic Chemistry*, 2012, (3):595-603; M. Li, et al, *Tetrahedron Letters*, 2009, 50(13):1478-1481; J. C. W. Evans, et al, *Organic Synthesis*, 1938, 18.

Other procedures include: Neumann K T, Lindhardt A T, Bang-Andersen B, Skrydstrup T, *Organic Letters*, 2015, 17:2094-2097; Tamba S, Okubo Y, Tanaka S, Monguchi D, *Journal of Organic Chemistry*, 2010, 75:6998-7001; Gu Z-S, Chen W-X, Shao L-X, *Journal of Organic Chemistry*, 2014, 79:5806-5811; Huang J, Chan J, Chen Y, Borths K D, et al, *Journal of the American Chemical Society*, 2010, 132:3674-3675; Boissarie P J, Hamilton Z E, Lang S, et al, *Organic Letters*, 2011, 13:6184-6187; Huang J, Chan J, Chen Y, *Journal of the American Chemical Society*, 2010, 132:3674-3675; Do H-Q, Daugulis O, *Journal of the American Chemical Society*, 2007, 129:12404-12405; Shen X-B, Chang Y, Chen W. X. et al, *Organic Letters*, 2014, 16:1984-1987.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3, 4-tetrahydronaphthalinyl (tetralinyl), indenyl and the like.

The term "one or more substituents" as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred bicyclic heteroaryl groups are nine- to fourteen-member rings that contain from one to three heteroatoms independently selected from oxygen, nitrogen, and sulfur. Examples of preferred bicyclic heteroaryl groups include benzimidazolyl, benzothiazolyl, benzoxazolyl, benzisoxazolyl, benzo[b]thiophenyl, indolyl, indazolinyl, quinolinyl, isoquinolinyl, quinazolinyl, quinoxalinyl, phthalazinyl, benzisothiazolyl and benzofuranyl, as well as the groups included in the definition of $X_1$ above.

The term "treating", as used herein, refers to reversing, alleviating, inhibiting the progress of, or preventing the disorder or condition to which such term applies, or preventing one or more symptoms of such disorder or condition. The term "treatment", as used herein, refers to the act of treating, as "treating" is defined immediately above.

The compounds of formula I of the present invention may also contain functional groups or heterocyclic ring systems that may exist in one or more tautomeric forms. The present invention includes within its scope all such tautomeric forms, including mixtures of such forms.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

Where cis- and trans-isomers are possible for an embodiment of the inventive compounds of formula I, both cis- and trans-isomers (i.e., diastereomers) are within the scope of this invention. Similarly, when R- and S-, or (+)- and (−)-, or d- and l-isomers (i.e., enantiomers) are possible for an embodiment of the inventive compounds of formula I, each and every one of said isomers are within the scope of this invention.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2$H, $^3$H, $^{11}$C, $^{13}$C, $^{14}$C, $^{13}$N, $^{15}$N, $^{17}$O, $^{18}$O, $^{35}$S, $^{31}$P, $^{32}$P, $^{31}$P, $^{18}$F and $^{37}$Cl, respectively. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and hence may be preferred in some circumstances. Isotopically labeled compounds of formula I of this invention and prodrugs thereof can generally be prepared by carrying out the procedures disclosed in the Schemes and/or the examples and Preparations below, by substituting a readily available isotopically labeled reagent for a non-isotopically labeled reagent.

Compounds of the present invention, prodrugs thereof, and pharmaceutically acceptable salts of said compounds, or of said prodrugs which contain the aforementioned isotopes and/or other isotopes of other atoms are within the scope of this invention.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buccal, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., HAT) is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to about 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of three days to three weeks, or until the condition is essentially controlled. Lower doses given less frequently can be used prophylactically to prevent or reduce the incidence of recurrence of the infection.

Aerosol formulations for treatment of the conditions referred to above (e.g., HAT) in the average human are preferably arranged such that each metered dose or "puff" of aerosol contains 0.1 micrograms to 100 micrograms of the compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving 1, 2 or 3 doses each time.

Examples of the disorders or conditions which may be treated by a compound, composition and method of this invention include: human African trypanosomiasis (HAT), Chagas disease, Leishmaniasis, toxoplasmosis or malaria.

As an example, the mammal in need of treatment or prevention may be a human. As another example, the mammal in need of treatment or prevention may be a mammal other than a human.

In so far as the compounds of formula I of this invention are basic compounds, they are capable of forming a variety of different salts with various inorganic and organic acids. Although such salts must be pharmaceutically acceptable for administration to animals, including humans, it is often desirable in practice to initially isolate the base compound from the reaction mixture as a pharmaceutically unacceptable salt, then isolate the base by treatment of the salt with an alkaline reagent and finally convert the isolated free base compound to a pharmaceutically acceptable acid addition salt.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, caproate, chloride, chlorobenzoate, citrate, dihydrogen phosphate, dinitrobenzoate, fumarate, glycollate, heptanoate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, gluconate, saccharate, nitrate and pamoate salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used are intended to have the following, general meaning:

bm: broad multiplet (NMR)
bs: broad singlet (NMR)
calcd.: calculated value
d: doublet (NMR)
dd: doublet of doublets (NMR)
d.e.: diatomaceous earth, filtering agent
equiv: equivalent
J: coupling constant (NMR)
LC: liquid chromatography
m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged homogeneous by thin layer chromatography and NMR.

Thin layer chromatography was performed on Kieselgel plates eluting with the indicated solvents, visualized by using a 254 nm UV lamp, and stained with an iodoplatinate spray (Sigma-Aldrich Chemical Co.). Preparatory chromatography was performed on Analtech Preparative Uniplates (20×20 cm, 2000 mm thick, UV, Silica G) purchased from ColeParmer, Vernon Hills, Ill. 60061, eluting with the indicated solvents and visualized by using a 254 nm UV lamp.

Nuclear Magnetic Resonance (NMR) spectra were acquired on either a 400 MHz or an 800 MHz Varian NMR Spectrometer (Varian Inc., Palo Alto, Calif.). Chemical shifts for hydrogen, carbon and nitrogen (i.e., $^1$H, $^{13}$C, $^{15}$N) NMR spectra are reported in parts per million (ppm) relative to the singlet of $CDCl_3$ at 7.24 ppm.

Liquid Chromatography was performed using a Teledyne-Isco CombiFlash Rf+ Lumen with RediSep Rf High Performance Gold, 12- or 24-gram, 40-60 micron silica, disposable flash columns.

Mass Spectrometry data were obtained on an Advion Expression$^s$ CMS (Advion Inc., Ithica, N.Y. 14850), in the mass range of 100-800 Daltons.

PREPARATION 1

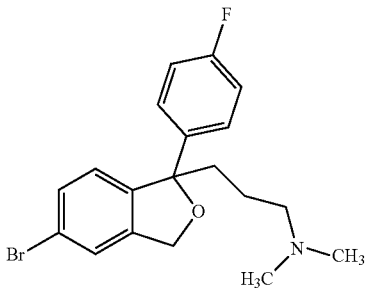

3-[5-bromo-1-(4-fluorophenyl)-1,3-dihydro-2-benzofuran-1-yl]-N,N-dimethyl-propan-1-amine (IV, where $R^1$ and $R^2$ are $CH_3$, $R^3$=H, $X_2$=4-F)

This compound was prepared according to the procedure of Zhang P, et al, *Journal of Medicinal Chemistry,* 2010, 53:6112-6121 and was isolated as a viscous oil.

Mass spectrum (m/z, %): 381, 380, 379, 378 ($m^{+1}$, 100%).

NMR (400 MHz, $CDCl_3$) δ 1.34 (m, 1H), 1.46 (m, 1H), 2.06-2.13 (m, 10H), 5.10 (dd, 2H), 6.97 (t, 2H), 7.13 (d, 1H), 7.31 (s, 1H), 7.42 (m, 3H).

Method A—Suzuki Coupling of Bromide (IV) and a Boronic Acid/Ester

Example 1

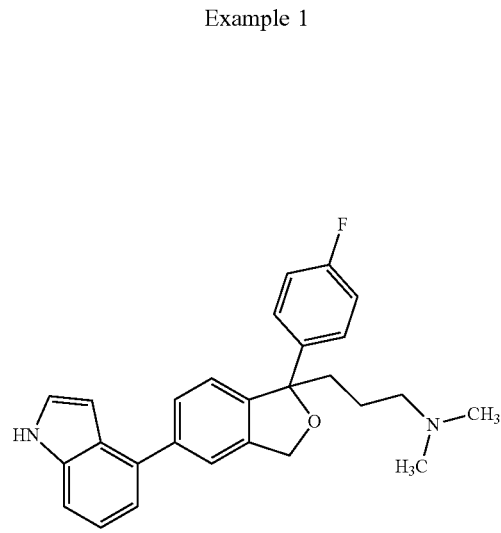

3-[1-(4-fluorophenyl)-5-(1H-indol-4-yl)-1,3-dihydro-2-benzofuran-1-yl]-N,N-dimethylpropan-1-amine 250 mg (0.66 mmol, MW=378) of 3-[5-bromo-1-(4-fluorophenyl)-1,3-dihydro-2-benzofuran-1-yl]-N,N-dimethylpropan-1-amine (IV, the title compound of Preparation 1) and 38 mg (0.033 mmol, MW=1156) of tetrakis-triphenylphosphine palladium(0) in 4.0 mL of dioxane was stirred at room temperature for 30 min. Next, 322 mg (1.32 mmol, MW=243, Sigma-Aldrich, St. Louis, Mo.) of 5-indolylboronic acid pinacol ester and 350 mg (23.2 mmol, MW=106) of $Na_2CO_3$ were added, followed by 1.0 mL of water. The reactants were stirred at 80-85° C. under $N_2$ for 4 hr, during which time the solution color changed from yellow to near black.

The reaction was worked up by separating the organic layer, washing it with water and then with saturated aqueous NaCl. The organic layer was next dried over $MgSO_4$, treated with darco and filtered through diatomaceous earth (d.e.). The solvent was removed in vacuo to give a pale brown solid. The solid was redissolved in ethyl acetate, heated until homogeneous, and allowed to slowly cool to room temperature at which point white crystals were observed and collected The crystals on tlc (90 EtOAc: 10 AcCN: 0.5 mL TEA) had Rf=0.35, whereas the filtrate contained mostly starting bromide. After drying under vacuum, the crystals melted to a black liquid at 220-225° C.

Yield of 60 mg (24%).

Mass spectrum (m/z, %): calcd. for $C_{27}H_{27}FN_2O$: $M^+$=414.51. Found: 415 ($M^{+1}$).

NMR (400 MHz, $CDCl_3$) δ 1.25 (s, 1H), 1.45 (bd, 2H), 2.00-2.35 (m, 9H), 5.25 (t, 2H), 6.65 (s, 1H), 7.0-7.6 (m, 7H), 8.4 (s, 1H).

Example 2

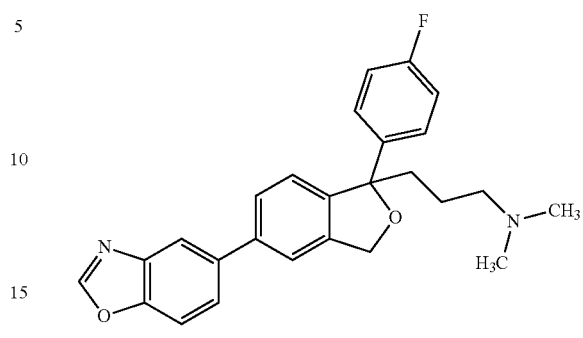

3-[1-(4-flurophenyl)-5-(1,3-benzoxazol-5-yl)-1,3-dihydro-2-benzofuran-1-yl]-N,N-dimethylpropan-1-amine In the same manner as Example 1, 175 mg (0.463 mmol, MW=378) of IV (Prep 1) in 4.0 mL dioxane was treated with 26 mg (0.0225 mmol, MW=1156) of $(PPh_3)_4Pd(0)$ at room temp for 30 min, followed by the addition of 227 mg (0.926 mmol, MW=245.1; Combi-Blocks, INC., San Diego, Calif., USA) of 1,3-benzoxazole-5-boronic acid pinacol ester and 245 mg (2.31 mmol, MW=106) of $Na_2CO_3$ with 1.0 mL $H_2O$. After heating at 80-85° C. under $N_2$ for 4 hr, the dark red solution was extracted in a separatory funnel with ethyl acetate. The organic layer was washed with $H_2O$ and saturated NaCl, dried over $MgSO_4$ and treated with Darco (activated charcoal). After filtration through a pad of diatomaceous earth (d.e.), the solvent was removed in vacuo to produce a crude oil.

The oil was chromatographed on a silica gel plate (2000 micron thickness, Analtech) and eluted with 90 EtOAc: 10 AcCN: 0.5 mL TEA. The silica gel band containing the product was scraped from the plate, and extracted with EtOAc. The EtOAc was filtered and concentrated in vacuo. Yield of 70 mg (40%) as a viscous oil.

Mass spectrum (m/z, %): Calcd. for $C_{26}H_{25}FN_2O_2$: $M^+$=416.487. Found: 417 ($M^{+1}$).

NMR (400 MHz, $CDCl_3$) δ 1.25 (s, 1H), 1.45 (bd, 2H), 2.00-2.35 (m, 8H), 5.25 (t, 2H), 7.05 (m, 1H), 7.35-7.60 (m, 8H), 7.9 (s, 1H), 8.15 (s, 1H).

Example 3

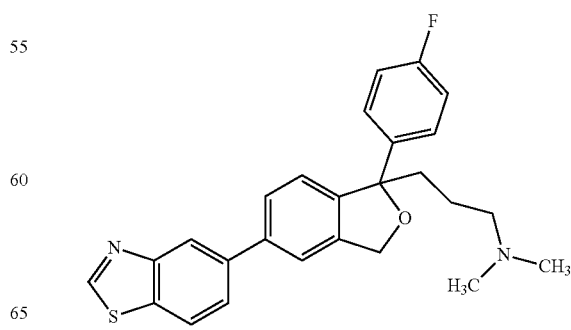

3-[1-(4-fluorophenyl)-5-(1,3-benzothiazol-5-yl)-1,3-dihydro-2-benzofuran-1-yl]-N,N-dimethylpropan-1-amine In the same manner as Example 1, 250 mg (0.66 mmol, MW=378) of IV in 4.0 mL dioxane was treated with 38 mg (0.033 mmol, MW=1156) of (PPh$_3$)$_4$Pd(0) at room temp for 30 min, followed by the addition of 345 mg (1.32 mmol, MW=261.1; Combi-Blocks, INC., San Diego, Calif., USA) of benzothiazole-5-boronic acid pinacol ester and 350 mg (3.3 mmol, MW=106) of Na$_2$CO$_3$ with 1.0 mL H$_2$O. After heating at 80-85° C. under N$_2$ for 4 hr, the dark red solution was extracted with EtOAc in a separatory funnel. The organic layer was washed with H$_2$O and saturated NaCl, dried over MgSO$_4$ and treated with Darco (activated charcoal). After filtration through a pad of d.e., the solvent was removed in vacuo to produce a crude oil.

The oil was chromatographed on a silica gel plate (2000 micron, Analtech) and eluted with 90 EtOAc: 10 AcCN: 0.5 mL TEA. The silica gel band containing the product was scraped from the plate, stirred and extracted with EtOAc. The EtOAc was filtered and concentrated in vacuo to a crude oil. Yield of 70 mg (40%) as a viscous oil.

Mass spectrum (m/z, %): Calcd. for C$_{26}$H$_{25}$FN$_2$OS: M$^+$=432.5. Found: 433 (M$^{+1}$).

NMR (400 MHz, CDCl$_3$) δ 1.25 (s, 1H), 1.45 (bd, 2H), 2.00-2.35 (m, 9H), 5.25 (t, 2H), 7.0 (t, 2H), 7.25-7.55 (m, 7H), 8.0 (s, 1H), 8.35 (s, 1H), 9.0 (s, 1H).

Example 4

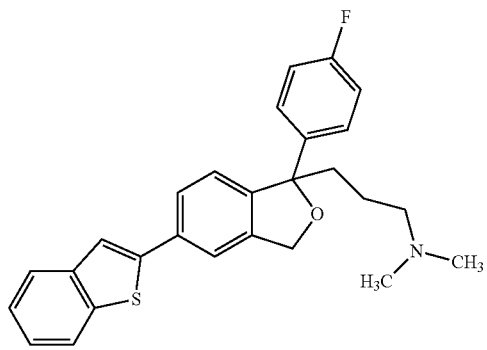 [SMILES: CN(C)CCCC1(c2ccc(F)cc2)OCc2cc(-c3cc4ccccc4s3)ccc21]

3-[1-(4-flurophenyl)]-5-[(1-benzo[b]thiophen-2-yl)]-1,3-dihydro-2-benzofuran-1-yl]-N,N-dimethylpropan-1-amine In the same manner as Example 1, 250 mg (0.66 mmol, MW=378) of IV in 4.0 mL dioxane was treated with 38 mg (0.033 mmol, MW=1155) of (PPh$_3$)$_4$Pd(0) at room temperature for 30 min, followed by the addition of 235 mg (1.18 mmol, MW=198.61) of benzo[b]thiophene-5-boronic acid (Tokyo Chemical Industry Co., Ltd. (TCI), Portland, Oreg., USA), and 350 mg (3.30 mmol, MW=106) of Na$_2$CO$_3$ with 1.0 mL H$_2$O. After heating at 80-85° C. under N$_2$ for 4 hr, the dark red solution was extracted with EtOAc in a separatory funnel. The organic layer was washing with H$_2$O and saturated NaCl, dried over MgSO$_4$ and treated with Darco (activated charcoal). After filtration through d.e., the solvent was removed in vacuo to produce a crude oil.

The oil was chromatographed on a silica gel plate (2000 micron, Analtech) and eluted with 90 EtOAc: 10 AcCN: 0.5 mL TEA. The silica gel band containing the product was scraped from the plate, stirred and extracted with EtOAc. The EtOAc was filtered and concentrated in vacuo to a crude oil which slowly crystallized. Yield of 70 mg (40%).

Mass spectrum (m/z): Calcd. for C$_{27}$H$_{26}$FNOS: M$^+$=431.56. Found: 432 (M$^{+1}$).

NMR (400 MHz, CDCl$_3$) δ 1.45 (bd, 2H), 1.80 (bs, 1H), 2.2 (m, 9H), 5.25 (t, 2H), 7.0 (t, 1H), 7.25-7.85 (m, 9H).

Example 5

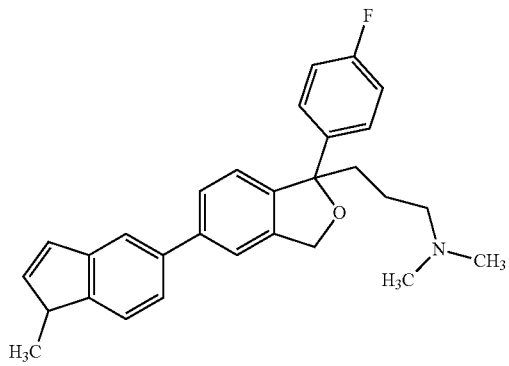 [SMILES: CC1C=Cc2cc(-c3ccc4c(c3)COC4(CCCN(C)C)c3ccc(F)cc3)ccc21]

3-[1-(4-fluorophenyl)]-[5-(1-methyl-1H-indol-5-yl)-1,3-dihydro-2-benzofuran-1-yl]-N,N-dimethylpropan-1-amine In the same manner as Example 1, 250 mg (0.66 mmol) of IV in 4.0 mL dioxane was treated with 38 mg (0.033 mmol, MW=1156) of (PPh$_3$)$_4$Pd(0) at room temp for 30 min, followed by the addition of 231 mg (1.32 mmol, MW=174.98; Frontier Scientific, Inc., Logan, Utah) of N-methylindole-5-boronic acid, and 245 mg (2.3 mmol, MW=106) of Na$_2$CO$_3$ with 1.0 mL H$_2$O. After heating at 80-85° C. for 4 hr, the dark red solution was extracted with EtOAc in a separatory funnel. The organic layer was washing with H$_2$O and saturated NaCl, dried over MgSO$_4$ and treated with Darco (activated charcoal). After filtration through a pad of d.e., the solvent was removed in vacuo to produce a crude oil.

The oil was chromatographed on a silica gel plate (2000 micron, Analtech) and eluted with 90 EtOAc: 10 AcCN: 0.5 mL TEA. The silica gel band containing the product was scraped from the plate, stirred and extracted with EtOAc. The EtOAc was filtered and concentrated in vacuo to a crude oil.

Yield of 30 mg (12.2%) as a viscous oil.

Mass spectrum (m/z, %): Calcd. for C$_{28}$H$_{29}$FN$_2$O: M$^+$=428.54. Found: 429 (M$^{+1}$).

NMR (400 MHz, CDCl$_3$) δ 1.3 (bs, 1H), 1.50 (bd, 2H), 2.2 (m, 8H), 2.4 (m, 2H), 3.85 (s, 3H), 5.25 (t, 2H), 6.55 (s, 1H), 7.05 (m, 2H), 7.35-7.55 (m, 7H), 7.80 (s, 1H).

Example 6

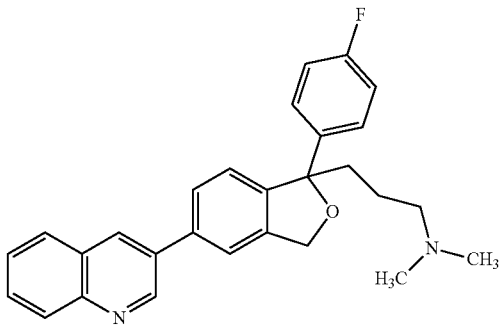 [SMILES: CN(C)CCCC1(c2ccc(F)cc2)OCc2cc(-c3cnc4ccccc4c3)ccc21]

3-[1-(4-fluorophenyl)]-[5-(quinolin-3-yl)-1,3-di-hydro-2-benzofuran-1-yl]-N,N-dimethylpropan-1-amine In the same manner as Example 1, 250 mg (0.066 mmol) of IV in 4.0 mL dioxane was treated with 38 mg (0.033 mmol, MW=1156) of (PPh$_3$)$_4$Pd(0) at room temp for 30 min, followed by the addition of 337 mg (1.32 mmol, MW=255.1; Combi-Blocks, INC., San Diego, Calif., USA) of quinoline-3-boronic acid pinacol ester, and 350 mg (3.3 mmol) of Na$_2$CO$_3$ with 1.0 mL H$_2$O. After heating at 80-85° C. for 4 hr under N$_2$, the dark red solution was extracted with EtOAc in a separatory funnel. The organic layer was washed with H$_2$O and saturated NaCl, dried over MgSO$_4$ and treated with Darco (activated charcoal). After filtration through a pad of d.e., the solvent was removed in vacuo to produce a crude oil.

The oil was chromatographed on a silica gel plate (2000 micron, Analtech) and eluted with 90 EtOAc: 10 AcCN: 0.5 mL TEA. The silica gel band containing the product was scraped from the plate, stirred and extracted with EtOAc. The EtOAc was filtered and concentrated in vacuo to a crude oil. Yield of 140 mg (56%) as a viscous oil.

Mass spectrum (m/z, %): Calcd. for C$_{28}$H$_{27}$FN$_2$O: M$^+$=426.54. Found: 427 (M$^{+1}$).

NMR (400 MHz, CDCl$_3$) δ 1.27 (s, 1H), 1.45 (bd, 2H), 1.80 (bs, 1H), 2.15-2.35 (m, 8H), 5.25 (t, 2H), 7.05 (t, 2H), 7.4-7.9 (m, 8H), 8.15 (s, 1H), 8.25 (s, 1H), 9.15 (s, 1H).

Example 7

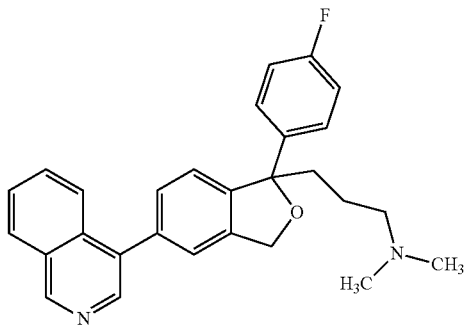 [SMILES: CN(C)CCCC1(c2ccc(F)cc2)OCc2cc(-c3cncc4ccccc34)ccc21]

3-[1-(4-fluorophenyl)]-[5-(isoquinolin-4-yl)-1,3-dihydro-2-benzofuran-1-yl]-N,N-dimethylpropan-1-amine In the same manner as Example 1, 250 mg (0.66 mmol) of IV in 4.0 mL dioxane was treated with 38 mg (0.033 mmol, MW=1156) of (PPh$_3$)$_4$Pd(0) at room temperature for 30 min, followed by the addition of 337 mg (1.32 mmol) of isoquinoline-4-boronic acid pinacol ester (Combi-Blocks, INC., San Diego, Calif., USA), and 245 mg (3.3 mmol) of Na$_2$CO$_3$ with 1.0 mL H$_2$O. After heating at 80-85° C. under N$_2$ for 4 hr, the dark red solution was extracted with ethyl acetate in a separatory funnel. The organic layer was washed with H$_2$O and saturated NaCl, dried over MgSO$_4$ and treated with Darco (activated charcoal). After filtration through a pad of d.e., the solvent was removed in vacuo to produce a crude oil.

The oil was chromatographed on a silica gel plate (2000 micron, Analtech) and eluted with 90 EtOAc: 10 AcCN: 0.5 mL TEA. The silica gel band containing the product was scraped from the plate, stirred and extracted with EtOAc. The EtOAc was filtered and concentrated in vacuo to a crude oil. Yield of 150 mg (60%) as a viscous oil.

Mass spectrum (m/z, %): Calcd. for C$_{28}$H$_{27}$FN$_2$O M$^+$=426.54. Found: 427 (M$^{+1}$).

NMR (400 MHz, CDCl$_3$) δ 1.45 (bd, 2H), 1.65 (bs, 1H), 2.2 (bs, 8H), 5.25 (t, 2H), 7.05 (t, 1H), 7.25-7.75 (m, 8H), 7.85 (d, 1H), 8.05 (d, 1H), 8.40 (s, 1H), 9.25 (s, 1H).

Method B—Reaction of Bromide (IV) and a Bicyclic Compound

Example 8

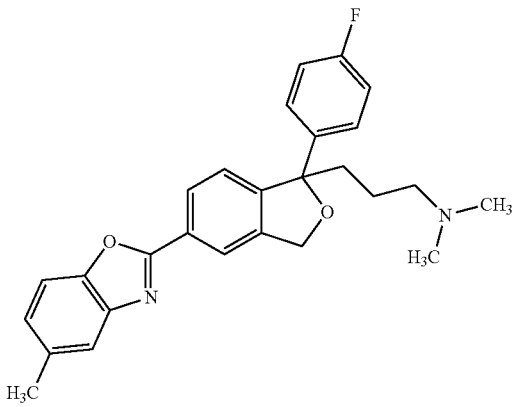 [SMILES: Cc1ccc2oc(-c3ccc4c(c3)COC4(CCCN(C)C)c3ccc(F)cc3)nc2c1]

3-[1-(4-fluorophenyl)-5-(5-methyl-1,3-benzoxazol-2-yl)-1,3-dihydro-2-benzofuran-1-yl]-N,N-dimethyl-propan-1-amine In a 50 mL round bottom flask, fitted with magnetic stir bar, reflux condenser and nitrogen inlet was placed 250 mg (0.66 mmol) of IV in 10 mL dimethylformamide (DMF). Under N$_2$, 153 mg (0.13 mmol, MW=1156) of (PPh$_3$)$_4$Pd(0) was added and the mixture was stirred for 30 min at room temperature. 5-Methyl-benzoxazole (88 mg, 0.66 mmol, MW=133.15; Sigma-Aldrich, St. Louis, Mo.), copper (I) iodide (252 mg, 1.32 mmol, MW=190.45) and cesium carbonate (430 mg, 1.32 mmol, MW=325.82) were added and the reactants were heated to 140° C. for 24 hr, during which time the color changed from yellow to black. The mixture was partitioned between ethyl acetate and water, the water layer was extracted with additional EtOAc and the combined organic layers were washed with water and saturated aqueous NaCl, dried with MgSO4, treated with Darco (activated charcoal) and filtered through celite (diatomaceous earth). The EtOAc was removed in vacuo to produce a crude oil. An L/C purification (90% EtOAc: 10% CH3OH: 0.5 mL triethylamine) provided the desired product as an oil. Yield of 15 mg (6%).

Mass spectrum (m/z, %): Calcd. for $C_{27}H_{27}FN_2O_2$, $M^+=430.51$. Found: 431 ($M^{+1}$).

Determination of Biological Activity

*T. brucei brucei* Assay

The growth inhibition assay for *T. brucei brucei* was conducted as described previously by Z. B. Mackey, et al (Kenny K. H. Ang, Joseline Ratnam, Jiri Gut, Jennifer Legac, Elizabeth Hansell, Zachary B. Mackey, Katarzyna M. Skrzypczynska, Anjan Debnath, Juan C. Engel, Philip J. Rosenthal, James H. McKerrow, Michelle R. Arkin, Adam R. Renslo (2011) "Mining a Cathepsin Inhibitor Library for New Antiparasitic Drug Leads", PLoS *Neglected Tropical Diseases*, 5(5):e1023). Bloodstream forms of the monomorphic *T. brucei brucei* clone 427-221a were grown in complete HMI-9 medium containing 10% FBS, 10% Serum Plus medium (Sigma Inc., St. Louis, Mo., USA), 50 U/mL penicillin and 50 mg/mL streptomycin (Invitrogen) at 37° C. under a humidified atmosphere and 5% $CO_2$. Inhibitor stocks were prepared in 100% DMSO and screened at 5 mM for percent inhibition values or serially diluted from 25 mM to 0.04 mM in 10% DMSO for IC50 determinations. 5 mL of each dilution was added to 95 mL of diluted parasites (16104 cells per well) in sterile Greiner 96-well flat white opaque culture plates such that the final DMSO concentration was 0.5%. The 0% inhibition control wells contained 0.5% DMSO while 100% inhibition control wells contained 50 mM thimerosal (Sigma). After compound addition, plates were incubated for 40 hours at 37° C. At the end of the incubation period, 50 mL of CellTiter-Glo™ reagent (Promega Inc., Madison, Wis., USA) was added to each well and plates were placed on an orbital shaker at room temperature for 2 min to induce lysis. After an additional 10 min of incubation without shaking to stabilize the signal, the ATP-bioluminescence of each well was determined using an Analyst HT plate reader (Molecular Devices, Sunnyvale, Calif., USA). Raw values were converted to log 10 and percentage inhibition calculated relative to the controls. IC50 curve fittings were performed with Prism 4 software as above. Pentamidine was used as a comparator in the assay.

DATA

| Example | IC50 (µM) |
|---------|-----------|
| 1 | 1.5 |
| 2 | 0.41 |
| 3 | 1.2 |
| 4 | 0.51 |
| 5 | 1.6 |
| 6 | 3.0 |
| 7 | 1.0 |
| 8 | 0.11 |

We claim:
1. A compound of the formula (I):

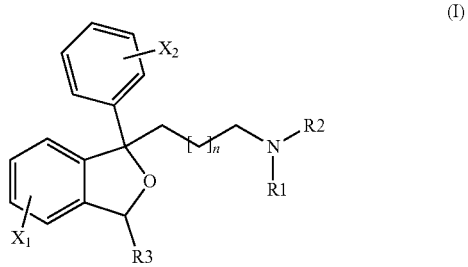

or the pharmaceutically acceptable salt(s) thereof, wherein:
   $X_1$ is bicyclic heteroaryl group selected from the list consisting of benzothiazolyl, benzoxazolyl, benzisoxazolyl, quinolinyl, quinazolinyl, quinoxalinyl, benzisothiazolyl and benzofuranyl;
   $X_2$ is H, Cl or F;
   R1 and R2 are independently hydrogen or methyl;
   R3 is hydrogen; and
   n is zero, one or two.

2. A compound of claim 1, wherein R1 and R2 are both methyl.

3. A compound of claim 1, wherein $X_2$ is 4-fluoro.

4. A compound of claim 1, wherein n is one.

5. A compound of claim 1, wherein $X_1$ is a heteroaryl group selected from the list consisting of benzothiazolyl, benzoxazolyl, benzisoxazolyl, quinolinyl, quinazolinyl, quinoxalinyl, benzisothiazolyl and benzofuranyl, and n is one or two.

6. A compound of formula I according to claim 1, wherein R1 is hydrogen, R2 is hydrogen, R3 is hydrogen, n is one and $X_2$ is fluoro.

7. A compound of formula I according to claim 1, wherein R1 is methyl and R2 is hydrogen.

8. A compound of formula I according to claim 1, wherein the compound is selected from:
   3-[1-(4-fluorophenyl)]-3-[5-(5-methyl-1,3-benzoxazol-2-yl)-1,3-dihydro-2-benzo-furan-1-yl]-N,N-dimethylpropan-1-amine;
   3-[1-(4-fluorophenyl)]-3-[5-(1,3-benzoxazol-5-yl)-1,3-dihydro-2-benzofuran-1-yl]-N,N-dimethylpropan-1-amine;
   3-[1-(4-fluorophenyl)]-3-[5-(1-benzothiazol-5-yl)-1,3-dihydro-2-benzofuran-1-yl]-N,N-dimethylpropan-1-amine; and
   3-[1-(4-fluorophenyl)]-3-[5-(quinolin-3-yl)-1,3-dihydro-2-benzofuran-1-yl]-N,N-dimethylpropan-1-amine.

9. A compound of formula I according to claim 1, wherein the compound is selected from:
   3-[1-(4-fluorophenyl)-5-(5-methyl-1,3-benzoxazol-2-yl)-1,3-dihydro-2-benzofuran-1-yl]-N,N-dimethylpropan-1-amine;
   3-[1-(4-fluorophenyl)-5-(5,6-dimethyl-1,3-benzoxazol-2-yl)-1,3-dihydro-2-benzofuran-1-yl]-N,N-dimethylpropan-1-amine;
   3-[1-(4-fluorophenyl)-5-(5-ethyl-1,3-benzoxazol-2-yl)-1,3-dihydro-2-benzofuran-1-yl]-N,N-dimethylpropan-1-amine;
   3-[1-(4-fluorophenyl)-5-(5-fluoro-1,3-benzoxazol-2-yl)-1,3-dihydro-2-benzofuran-1-yl]-N,N-dimethylpropan-1-amine;

3-[1-(4-fluorophenyl)-5-(5-trifluoromethyl-1,3-benzox-azol-2-yl)-1,3-dihydro-2-benzofuran-1-yl]-N,N-dimethylpropan-1-amine;
3-[1-(4-fluorophenyl)-5-(5-methoxy-1,3-benzoxazol-2-yl)-1,3-dihydro-2-benzofuran-1-yl]-N,N-dimethylpropan-1-amine;
3-[1-(4-fluorophenyl)-5-(2-methyl-1,3-benzothiazol-5-yl)-1,3-dihydro-2-benzofuran-1-yl]-N,N-dimethylpropan-1-amine;
3-[1-(4-fluorophenyl)-5-(2-phenyl-1,3-benzothiazol-5-yl)-1,3-dihydro-2-benzofuran-1-yl]-N,N-dimethylpropan-1-amine;
3-[1-(4-fluorophenyl)-5-(6,7-dimethyl-1,3-benzothiazol-5-yl)-1,3-dihydro-2-benzofuran-1-yl]-N,N-dimethylpropan-1-amine;
3-[1-(4-fluorophenyl)-5-(7-nitro-1,3-benzothiazol-5-yl)-1,3-dihydro-2-benzofuran-1-yl]-N,N-dimethylpropan-1-amine;
3-[1-(4-fluorophenyl)-5-(1,3-benzothiazol-5-yl)-1,3-dihydro-2-benzo-furan-1-yl]-N,N-methylpropan-1-amine;
3-[1-(4-fluorophenyl)-5-(6-trifluoromethyl-1,3-benzoxazol-5-yl)-1,3-dihydro-2-benzofuran-1-yl]-N,N-dimethylpropan-1-amine;
3-[1-(4-fluorophenyl)-5-(6-methoxy-1,3-benzoxazol-5-yl)-1,3-dihydro-2-benzofuran-1-yl]-N,N-dimethylpropan-1-amine;
3-[1-(4-fluorophenyl)-5-(4,7-dimethyl-1,3-benzoxazol-5-yl)-1,3-dihydro-2-benzofuran-1-yl]-N,N-dimethylpropan-1-amine;
3-[1-(4-fluorophenyl)-5-(6-chloro-1,3-benzoxazol-5-yl)-1,3-dihydro-2-benzofuran-1-yl]-N,N-dimethylpropan-1-amine;
3-[1-(4-fluorophenyl)-5-(6-fluoro-1,3-benzoxazol-5-yl)-1,3-dihydro-2-benzofuran-1-yl]-N,N-dimethylpropan-1-amine;
3-[1-(4-fluorophenyl)]-[5-(quinolin-3-yl)-1,3-dihydro-2-benzofuran-1-yl]-N,N-dimethylpropan-1-amine;
3-[1-(4-fluorophenyl)]-[5-(2-methyl-quinolin-3-yl)-1,3-dihydro-2-benzofuran-1-yl]-N,N-dimethylpropan-1-amine;
3-[1-(4-fluorophenyl)]-[5-(6,7-dichloro-quinolin-3-yl)-1,3-dihydro-2-benzofuran-1-yl]-N,N-dimethylpropan-1-amine;
3-[1-(4-fluorophenyl)]-[5-(7,8-dimethoxy-quinolin-3-yl)-1,3-dihydro-2-benzofuran-1-yl]-N,N-propan-1-amine;
3-[1-(4-fluorophenyl)]-[5-(7-methyl-quinolin-3-yl)-1,3-dihydro-2-benzofuran-1-yl]-N,N-methylpropan-1-amine;
3-[1-(4-fluorophenyl)]-[5-(7-nitro-quinolin-3-yl)-1,3-dihydro-2-benzofuran-1-yl]-N,N-dimethylpropan-1-amine;
3-[1-(4-fluorophenyl)-5-(1,2-benzisoxazol-3-yl)-1,3-dihydro-2-benzofuran-1-yl]-N,N-dimethylpropan-1-amine;
3-[1-(4-fluorophenyl)-5-(1,2-benzisoxazol-5-yl)-1,3-dihydro-2-benzofuran-1-yl]-N,N-dimethylpropan-1-amine;
3-[1-(4-fluorophenyl)-5-(1,3-quinazol-2-yl)-1,3-dihydro-2-benzofuran-1-yl]-N,N-dimethylpropan-1-amine;
3-[1-(4-fluorophenyl)-5-(1,3-quinazol-4-yl)-1,3-dihydro-2-benzofuran-1-yl]-N,N-dimethylpropan-1-amine;
3-[1-(4-fluorophenyl)-5-(1,3-quinazol-6-yl)-1,3-dihydro-2-benzofuran-1-yl]-N,N-dimethylpropan-1-amine;
3-[1-(4-fluorophenyl)-5-(1,3-quinazol-7-yl)-1,3-dihydro-2-benzofuran-1-yl]-N,N-dimethylpropan-1-amine;
3-[1-(4-fluorophenyl)-5-(1,4-quinoxalin-2-yl)-1,3-dihydro-2-benzofuran-1-yl]-N,N-dimethylpropan-1-amine;
3-[1-(4-fluorophenyl)-5-(1,4-quinoxalin-6-yl)-1,3-dihydro-2-benzofuran-1-yl]-N,N-dimethylpropan-1-amine;
3-[1-(4-fluorophenyl)-5-(1,4-quinoxalin-7-yl)-1,3-dihydro-2-benzofuran-1-yl]-N,N-dimethylpropan-1-amine;
3-[1-(4-fluorophenyl)-5-(1,2-benzisothiazol-3-yl)-1,3-dihydro-2-benzofuran-1-yl]-N,N-dimethylpropan-1-amine;
3-[1-(4-fluorophenyl)-5-(1,2-benzisothiazol-5-yl)+1,3-dihydro-2-benzofuran-1-yl]-N,N-dimethylpropan-1-amine;
3-[1-(4-fluorophenyl)-5-(1,2-benzisothiazol-6-yl)+1,3-dihydro-2-benzofuran-1-yl]-N,N-dimethylpropan-1-amine; and
3-[1-(4-fluorophenyl)-5-(1,2-benzisothiazol-7-yl)+1,3-dihydro-2-benzofuran-1-yl]-N,N-dimethylpropan-1-amine.

10. A pharmaceutical composition comprising a compound of formula I as described in claim 1, or a pharmaceutically acceptable salt thereof, and a pharmaceutically acceptable carrier.

11. A method of treatment of a disorder or condition selected from the group consisting of human African trypanosomiasis, Chagas disease, Leishmaniasis, toxoplasmosis and malaria, the method comprising administering to a mammal in need of such treatment an amount of a compound of formula I, or a pharmaceutically acceptable salt thereof, as described in claim 1, that is effective in treating such disorder or condition.

12. The method of claim 11 wherein the mammal is a human.

13. A method of treatment of a disorder or condition selected from the group consisting of human African trypanosomiasis, Chagas disease, Leishmaniasis, toxoplasmosis and malaria, the method comprising administering to a mammal in need of such treatment an amount of a compound of formula I,

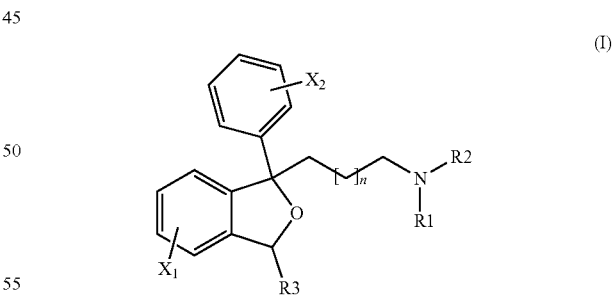

(I)

where $X_1$ is selected from the group consisting of benzothiophenyl, indolyl, indazolyl, phthalazinyl and isoquinolinyl, or a pharmaceutically acceptable salt thereof, as described in claim 1, that is effective in treating such disorder or condition.

14. The method of claim 13 wherein the mammal is a human.

15. A method of treatment of a disorder or condition selected from the group consisting of human African trypanosomiasis, Chagas disease, Leishmaniasis, toxoplasmosis and malaria, the method comprising administering to a mammal in need of such treatment an amount of a compound of formula I,

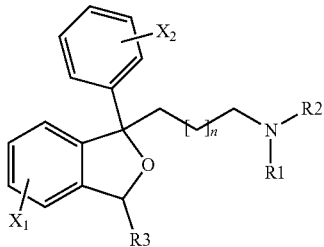

(I)

selected from the list consisting of:
3-[1-(4-fluorophenyl)]-3-[5-(5-methyl-1,3-benzoxazol-2-yl)-1,3-dihydro-2-benzo-furan-1-yl]-N,N-dimethylpropan-1-amine;
3-[1-(4-fluorophenyl)]-3-[5-(1,3-benzoxazol-5-yl)-1,3-dihydro-2-benzofuran-1-yl]-N,N-dimethylpropan-1-amine; and
3-[1-(4-fluorophenyl)]-3-[5-(quinolin-3-yl)-1,3-dihydro-2-benzofuran-1-yl]-N,N-dimethylpropan-1-amine,
or a pharmaceutically acceptable salt thereof, that is effective in treating such disorder or condition.

16. A method of treatment of a disorder or condition selected from the group consisting of human African trypanosomiasis, Chagas disease, Leishmaniasis, toxoplasmosis and malaria, the method comprising administering to a mammal in need of such treatment an amount of a compound of formula I,

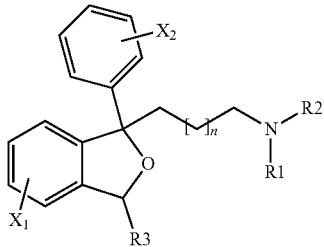

(I)

selected from the list consisting of:
3-[1-(4-fluorophenyl)-5-(5-methyl-1,3-benzoxazol-2-yl)-1,3-dihydro-2-benzofuran-1-yl]-N,N-dimethylpropan-1-amine;
3-[1-(4-fluorophenyl)-5-(5,6-dimethyl-1,3-benzoxazol-2-yl)-1,3-dihydro-2-benzofuran-1-yl]-N,N-dimethylpropan-1-amine;
3-[1-(4-fluorophenyl)-5-(5-ethyl-1,3-benzoxazol-2-yl)-1,3-dihydro-2-benzofuran-1-yl]-N,N-dimethylpropan-1-amine;
3-[1-(4-fluorophenyl)-5-(5-fluoro-1,3-benzoxazol-2-yl)-1,3-dihydro-2-benzofuran-1-yl]-N,N-dimethylpropan-1-amine;
3-[1-(4-fluorophenyl)-5-(5-trifluoromethyl-1,3-benzoxazol-2-O-1,3-dihydro-2-benzofuran-1-yl]-N,N-dimethylpropan-1-amine;
3-[1-(4-fluorophenyl)-5-(5-methoxy-1,3-benzoxazol-2-yl)-1,3-dihydro-2-benzofuran-1-yl]-N,N-dimethylpropan-1-amine;
3-[1-(4-fluorophenyl)-5-(2-methyl-1,3-benzothiazol-5-yl)-1,3-dihydro-2-benzofuran-1-yl]-N,N-dimethylpropan-1-amine;
3-[1-(4-fluorophenyl)-5-(2-phenyl-1,3-benzothiazol-5-yl)-1,3-dihydro-2-benzofuran-1-yl]-N,N-dimethylpropan-1-amine;
3-[1-(4-fluorophenyl)-5-(6,7-dimethyl-1,3-benzothiazol-5-yl)-1,3-dihydro-2-benzofuran-1-yl]-N,N-dimethylpropan-1-amine;
3-[1-(4-fluorophenyl)-5-(7-nitro-1,3-benzothiazol-5-yl)-1,3-dihydro-2-benzofuran-1-yl]-N,N-dimethylpropan-1-amine;
3-[1-(4-fluorophenyl)-5-(1,3-benzothiazol-5-yl)-1,3-dihydro-2-benzo-furan-1-yl]-N,N-methylpropan-1-amine;
3-[1-(4-fluorophenyl)-5-(6-trifluoromethyl-1,3-benzoxazol-5-yl)-1,3-dihydro-2-benzofuran-1-yl]-N,N-dimethylpropan-1-amine;
3-[1-(4-fluorophenyl)-5-(6-methoxy-1,3-benzoxazol-5-yl)-1,3-dihydro-2-benzofuran-1-yl]-N,N-dimethylpropan-1-amine;
3-[1-(4-fluorophenyl)-5-(4,7-dimethyl-1,3-benzoxazol-5-yl)-1,3-dihydro-2-benzofuran-1-yl]-N,N-dimethylpropan-1-amine;
3-[1-(4-fluorophenyl)-5-(6-chloro-1,3-benzoxazol-5-yl)-1,3-dihydro-2-benzofuran-1-yl]-N,N-dimethylpropan-1-amine;
3-[1-(4-fluorophenyl)-5-(6-fluoro-1,3-benzoxazol-5-yl)-1,3-dihydro-2-benzofuran-1-yl]-N,N-dimethylpropan-1-amine;
3-[1-(4-fluorophenyl)]-[5-(quinolin-3-yl)-1,3-dihydro-2-benzofuran-1-yl]-N,N-dimethylpropan-1-amine;
3-[1-(4-fluorophenyl)]-[5-(2-methyl-quinolin-3-yl)-1,3-dihydro-2-benzofuran-1-yl]-N,N-dimethylpropan-1-amine;
3-[1-(4-fluorophenyl)]-[5-(6,7-dichloro-quinolin-3-yl)-1,3-dihydro-2-benzofuran-1-yl]-N,N-dimethylpropan-1-amine;
3-[1-(4-fluorophenyl)]-[5-(7,8-dimethoxy-quinolin-3-yl)-1,3-dihydro-2-benzofuran-1-yl]-N,N-propan-1-amine;
3-[1-(4-fluorophenyl)]-[5-(7-methyl-quinolin-3-yl)-1,3-dihydro-2-benzofuran-1-yl]-N,N-methylpropan-1-amine;
3-[1-(4-fluorophenyl)]-[5-(7-nitro-quinolin-3-yl)-1,3-dihydro-2-benzofuran-1-yl]-N,N-dimethylpropan-1-amine;
3-[1-(4-fluorophenyl)-5-(1,2-benzisoxazol-3-yl)-1,3-dihydro-2-benzofuran-1-yl]-N,N-dimethylpropan-1-amine;
3-[1-(4-fluorophenyl)-5-(1,2-benzisoxazol-5-yl)-1,3-dihydro-2-benzofuran-1-yl]-N,N-dimethylpropan-1-amine;
3-[1-(4-fluorophenyl)-5-(1,2-indazol-3-yl)-1,3-dihydro-2-benzofuran-1-yl]-N,N-dimethylpropan-1-amine;
3-[1-(4-fluorophenyl)-5-(1,2-indazol-5-yl)-1,3-dihydro-2-benzofuran-1-yl]-N,N-dimethylpropan-1-amine;
3-[1-(4-fluorophenyl)-5-(1,2-indazol-6-yl)-1,3-dihydro-2-benzofuran-1-yl]-N,N-dimethylpropan-1-amine;
3-[1-(4-fluorophenyl)-5-(1,3-quinazol-2-yl)-1,3-dihydro-2-benzofuran-1-yl]-N,N-dimethylpropan-1-amine;

3-[1-(4-fluorophenyl)-5-(1,3-quinazol-4-yl)-1,3-dihydro-2-benzofuran-1-yl]-N,N-dimethylpropan-1-amine;
3-[1-(4-fluorophenyl)-5-(1,3-quinazol-6-yl)-1,3-dihydro-2-benzofuran-1-yl]-N,N-dimethylpropan-1-amine;
3-[1-(4-fluorophenyl)-5-(1,3-quinazol-7-yl)-1,3-dihydro-2-benzofuran-1-yl]-N,N-dimethylpropan-1-amine;
3-[1-(4-fluorophenyl)-5-(1,4-quinoxalin-2-yl)-1,3-dihydro-2-benzofuran-1-yl]-N,N-dimethylpropan-1-amine;
3-[1-(4-fluorophenyl)-5-(1,4-quinoxalin-6-yl)-1,3-dihydro-2-benzofuran-1-yl]-N,N-dimethylpropan-1-amine;
3-[1-(4-fluorophenyl)-5-(1,4-quinoxalin-7-yl)-1,3-dihydro-2-benzofuran-1-yl]-dimethylpropan-1-amine;
3-[1-(4-fluorophenyl)-5-(1,2-benzisothiazol-3-yl)-1,3-dihydro-2-benzofuran-1-yl]-N,N-dimethylpropan-1-amine;
3-[1-(4-fluorophenyl)-5-(1,2-benzisothiazol-5-yl)-)-1,3-dihydro-2-benzofuran-1-yl]-N,N-dimethylpropan-1-amine;
3-[1-(4-fluorophenyl)-5-(1,2-benzisothiazol-6-yl)+1,3-dihydro-2-benzofuran-1-yl]-N,N-dimethylpropan-1-amine; and
3-[1-(4-fluorophenyl)-5-(1,2-benzisothiazol-7-yl)-)-1,3-dihydro-2-benzofuran-1-yl]-N,N-dimethylpropan-1-amine, or a pharmaceutically acceptable salt thereof, that is effective in treating such disorder or condition.

* * * * *